United States Patent
Nakamura et al.

(10) Patent No.: US 6,835,325 B1
(45) Date of Patent: Dec. 28, 2004

(54) CROSSLINKING AGENT BASED ON POLYALLYL ETHER COMPOUND

(75) Inventors: Shin-ichiro Nakamura, Osaka (JP); Yasumi Shimizu, Osaka (JP); Tohru Matsutomi, Osaka (JP)

(73) Assignee: Daiso Co., Ltd., Osaka (JP)

( * ) Notice: Subject to any disclaimer, the term of this patent is extended or adjusted under 35 U.S.C. 154(b) by 466 days.

(21) Appl. No.: 10/111,014

(22) PCT Filed: Oct. 17, 2000

(86) PCT No.: PCT/JP00/07183

§ 371 (c)(1),
(2), (4) Date: Apr. 19, 2002

(87) PCT Pub. No.: WO01/29132

PCT Pub. Date: Apr. 26, 2001

(30) Foreign Application Priority Data

Oct. 21, 1999 (JP) .......................................... 11/299555
Oct. 21, 1999 (JP) .......................................... 11/299556

(51) Int. Cl.[7] ...................... C08F 120/06; C08F 120/10; C08F 118/02; C07C 41/00; C07C 43/15
(52) U.S. Cl. ........................... 252/182.18; 252/182.23; 252/182.24; 252/182.27; 526/317.1; 526/318; 526/320; 526/321; 526/328.5; 568/606; 568/673; 568/675; 568/688; 568/689
(58) Field of Search ...................... 252/182.13, 182.18, 252/182.19, 182.23, 182.24, 182.27, 183.11; 526/317.1, 318, 320, 321, 328.5; 568/606, 673, 675, 688, 689

(56) References Cited

U.S. PATENT DOCUMENTS

| | | | | |
|---|---|---|---|---|
| 5,010,154 A | * | 4/1991 | Hardiman | 526/135 |
| 5,095,069 A | * | 3/1992 | Ambrose et al. | 524/591 |
| 5,629,395 A | * | 5/1997 | Fujikake et al. | 526/238.23 |
| 6,130,304 A | * | 10/2000 | Sumiya et al. | 526/317.1 |
| 6,254,990 B1 | * | 7/2001 | Ishizaki et al. | 428/402 |
| 6,297,335 B1 | * | 10/2001 | Funk et al. | 526/317.1 |
| 6,414,214 B1 | * | 7/2002 | Engelhardt et al. | 604/368 |
| 6,538,059 B1 | * | 3/2003 | Muller et al. | 524/591 |
| 6,770,702 B1 | * | 8/2004 | Muller et al. | 524/539 |
| 2002/0128618 A1 | * | 9/2002 | Frenz et al. | 604/368 |
| 2002/0165288 A1 | * | 11/2002 | Frenz et al. | 521/50 |
| 2003/0144386 A1 | * | 7/2003 | Pakusch et al. | 524/5 |
| 2004/0077796 A1 | * | 4/2004 | Daniel et al. | 525/360 |

FOREIGN PATENT DOCUMENTS

| | | | |
|---|---|---|---|
| GB | 1 034 816 | * | 7/1966 |
| JP | 3-174414 | | 7/1991 |
| JP | 4-246403 | | 9/1992 |
| JP | 5-230160 | | 9/1993 |
| JP | 10-128108 | | 5/1998 |
| WO | 94/00214 | | 1/1994 |

OTHER PUBLICATIONS

English Language Abstract of JP2001122922, Nakamura et al. published May 8, 2001, Abstract data supplied from esp@cenet database–12.*

Smith et al., J.Polym. Sci. A: Polym. Chem., 35, pp. 799–806 (1997).

* cited by examiner

Primary Examiner—Joseph D. Anthony
(74) Attorney, Agent, or Firm—Wenderoth, Lind & Ponack, L.L.P.

(57) ABSTRACT

A crosslinking agent containing a polyallyl ether compound having at least one hydroxyl group derived from a glycidyl group and at least two allyl groups can be used for the production of a highly water-absorbing polymer comprising a polymerizable compound having a carbon-carbon double bond or a salt thereof, has a high solubility in aqueous solution of the monomer and gives a highly water-absorbing polymer having water absorptivity required at practical levels.

10 Claims, No Drawings

CROSSLINKING AGENT BASED ON POLYALLYL ETHER COMPOUND

FIELD OF THE INVENTION

The present invention relates to a crosslinking agent for use in the production of a highly water-absorbing polymer crosslinked in an aqueous medium and comprising a polymerizable compound having a carbon-carbon double bond or a salt thereof.

RELATED ART

Most of highly water-absorbing polymers comprising polymerizable compounds having polymerizable double bonds (e.g. carbon-carbon double bonds) or salts thereof are based on acrylate salt polymers and produced mainly by polymerization in an aqueous solution. It is proposed to use a wide variety of materials having a reactive double bond, such as acrylate esters, acrylic amides and allyl ethers, as crosslinking agents for crosslinking the highly water-absorbing polymers, It is reported that particularly when allyl compounds are used as the crosslinking agent, the polymers excellent particularly in water absorptivity can be obtained. Further, the reverse-phase suspension polymerization mathod polymerizing a monomer and a crosslinking agent dissolved in water suspended in an organic solvent is also industrially carried out, and this reverse-phase suspension polymerization method can also be regarded as the polymerization in an aqueous medium.

For example, it is reported in J. Polym. Sci. A: Polym. Chem. 35, 799 (1977) that polymers obtained by using polyethylene glycol diallyl ether as the crosslinking agent is superior in water absorptivity to the polymers obtained by using an acrylic crosslinking agent. However, the performance of the polyethylene glycol diallyl ether as the crosslinking agent is not satisfactory.

A method of neutralizing polymers obtained by polymerizing acrylic acid is known. JP-A-3-174414, which uses this method, discloses use of tetra-allyloxy ethane as a specific allyl compound. However, this compound suffers from problems such as deficient heat resistance, poor solubility in an aqueous solution of a monomer, and insufficient resistance to hydrolysis. Thus there is demand for development of crosslinking agents having higher performance.

Further, JP-A-4-246403 discloses use of triallyl amine, trially cyanurate, triallyl isocyanurate and triallyl phosphate. However, these crosslinking agents generally have problems such as deficient heat resistance, adverse effects on polymerization reaction, poor solubility in an aqueous solution of a monomer, and insufficient resistance to hydrolysis, and thus none of these crosslinking agents are practical.

Generally in the aqueous solution polymerization, an aqueous solution of an acrylic acid monomer is neutralized at a degree of about 75% with e.g. an aqueous solution of sodium hydroxide, then a crosslinking agent is mixed therewith, the monomer is polymerized by a polymerization initiator, and the formed solid is cut into pieces of suitable size and then dried (hereinafter, this method is referred to as "method of polymerization after neutralization"). On the other hand, the crosslinking agent is dissolved in an aqueous solution of acrylic acid, and the solid formed by polymerization is cut and neutralized (hereinafter, this method is referred to as "method of polymerization before neutralization"). This method is disadvantageous in production efficiency and uneven neutralization of the product, in comparison with the neutralization in solution form.

SUMMARY OF THE INVENTION

The object of the present invention is to provide a novel allyl type crosslinking agent soluble in an aqueous solution of a monomer (e.g., an aqueous solution of an acrylate salt) and free of the problems possessed by the prior arts, in order to produce a highly water-absorbing polymer having water-absorptivity required at practical levels.

The present invention provides a crosslinking agent for use in the production of a highly water-absorbing polymer comprising a polymerizable compound having a carbon-carbon double bond or a salt thereof, comprising a polyallyl ether compound having at least two allyl groups and at least one hydroxyl group derived from a glycidyl group.

DETAILED EXPLANATION OF THE INVENTION

In the present invention, the polyallyl ether compound is used as a crosslinking agent for the production of highly water-absorbing polymers. The crosslinking agent comprises one polyallyl ether compound or a mixture of at least two polyallyl ether compounds.

A molecule of the polyallyl ether compound has at least one hydroxyl group derived from a glycidyl group and at least two allyl groups. The number of hydroxyl groups is at least one, for example at least two, and specific example of the number of hydroxyl groups is from 1 to 10, particularly from 1 to 4. The number of allyl groups is at least 2, for example at least 3, specifically from 3 to 8. In the case of the mixture of polyallyl ether compounds, an average number of hydroxyl groups is at least 0.5, for example at least 1.0, particularly at least 1.5, and an average number of allyl groups is at least 2.0, for example at least 2.5, particularly at least 3.0. The numbers of hydroxyl groups and allyl groups (including the average numbers thereof) are determined by NMR (particularly, $^1$H NMR).

The polyallyl ether compound may have or may not have an oxyethylene chain.

The polyallyl ether compound may be:

(A-1) a polyallyl ether compound having at least two allyl groups and at least one hydroxyl group derived from a glycidyl group, and having no oxyethylene chain, and/or (A-2) a polyallyl ether compound having at least two allyl groups and at least one hydroxyl group derived from a glycidyl group, and having at least one oxyethylene chain.

Hereinafter, the polyallyl ether compound (A-1) having no oxyethylene chain is explained.

The polyallyl ether compound (A-1) having no oxyethylene chain is preferably a compound of the general formula (I):

$$R^1-OC(R^3)_2-C(R^3)(OH)-C(R^3)_2\,O-R^2 \qquad (I)$$

wherein

R$^1$ and R$^2$ are, the same or different, an allyl group, or a hydrocarbon group (the number of carbon atoms in the hydro-carbon group is from 1 to 15) having an allyl group and optionally having an ether oxygen atom and/or a hydroxyl group, and each R$^3$ is, the same or different, a hydrogen atom, a linear or branched alkyl group having 1 to 10 carbon atoms or a halogen atom. All of R$^3$ group may be a hydrogen atom.

The polyallyl ether compound (A-1) having no oxyethylene chain may be, for example, $$R^{11}(OA)_n(OH)_j\text{—OCH}_2\text{CH(OH)CH}_2\text{ O-A} \quad (I\text{-}1)$$

or $$R^{11}(OA)_n(OH)_j\text{—OCH}_2\text{CH(OH)CH}_2\text{ O—}(OA)_k(OH)_mR^{12} \quad (I\text{-}2)$$

wherein $R^{11}$ and $R^{12}$ is a $C_2$–$C_{12}$ (for example, $C_4$–$C_{12}$, particularly $C_4$–$C_{10}$)
hydrocarbon group optionally having an ether oxygen atom, A is an allyl group, n and k are a number of at least 1, and j and m is a number of at least 0.

$R^{11}$ is an organic group having a valency of (n+j+1), and $R^{12}$ is an organic group having a valency of (m+k+1). The number of the OH groups in the polyallyl ether compound may be 1.

The polyallyl ether compound (A-1) having no oxyethylene chain can be prepared by reacting an epoxy compound with an allyl group-containing alcohol. An epoxy group in the epoxy compound reacts with a hydroxyl group in the allyl group-containing alcohol to give the polyallyl ether compound.

The epoxy compound may be an epoxy compound of the general formula:

$$G\text{-O-A} \quad (i)$$

or the general formula:

$$G\text{-O—}R^{12}(OA)_k(OH)_m \quad (ii)$$

wherein

G is a glycidyl group, $R^{12}$ is a $C_4$–$C_{12}$ hydrocarbon group optionally having an ether oxygen atom, A is an allyl group, k is a number of at least 1, and m is a number of at least 0.

The allyl group-containing alcohol may be an alcohol of the general formula:

$$R^{11}(OA)_n(OH)_{j+1}$$

wherein $R^{11}$ is a $C_4$–$C_{12}$ hydrocarbon group optionally having an ether oxygen atom, A is an allyl group, n is a number of at least 1, and j is a number of at least 0.

In one of embodiments of the present invention, the polyallyl ether compound (A-1) having no oxyethylene chain is of the general formula:

$$R^{61}(OA)_n(OH)_jOC(R^{62}\ (OH)C(R^{62})_2OA$$

wherein $R^{61}$ a linear or branched $C_1$–$C_{12}$ hydrocarbon group optionally intervened by an ether oxygen atom, each $R^{62}$ is, the same or different, a hydrogen atom, a linear or branched $C_1$–$C_{10}$ alkyl group, or a halogen atom, A is an allyl group, n is a number of at least 1, and j is a number of at least 0.

For example, the polyally ether compound can be prepared by reacting an allyl group-containing epoxy compound of the general formula:

$$GOA$$

wherein

G is a glycidyl group, and

A is an allyl group, with an allyl group-containing alcohol of the general formula:

$$R^{61}(OA)_n(OH)_{x-n}$$

wherein $R^{61}$ a linear or branched $C_1$–$C_{10}$ hydrocarbon group optionally intervened by an ether oxygen atom, A is an allyl group, x is a whole number of at least 2, and n is a whole number of from 1 to (x-1), said allyl group-containing alcohol being prepared by the allyl-etherifying reaction of a polyol of the general formula:

$$R^{61}(OH)_x$$

wherein $R^{61}$ and x is the same as defined above.

x may be, for example, from 2 to 10, particularly from 2 to 6. j is at least 0, for example, from 0 to 8. n is at least 1, particularly at least 2, for example, from 2 to 5. Preferable examples of n are 1, 2, 3, 4 and 5.

Specific examples of $R^{61}(OH)_x$ are ethylene glycol, glycerin, erythritol, xylitol, sorbitol, trimethylolpropane, pentaerythritol and dipentaerythrytol.

Specific examples of such polyallyl ether compound (that is, reaction product between $R^{61}(OA)_n(OH)_{x-n}$ and GOA) are as as follows:

a reaction product between ethyleneglycol monoallyl ether and allyl glycidyl ether, a reaction product between glycerin monoallyl ether and allyl glycidyl ether, a reaction product between erythritol diallyl ether and allyl glycidyl ether, a reaction product between erythritol triallyl ether and allyl glycidyl ether, a reaction product between xylitol diallyl ether and allyl glycidyl ether, a reaction product between xylitol triallyl ether and allyl glycidyl ether, a reaction product between xylitol tetraallyl ether and allyl glycidyl ether, a reaction product between sorbitol diallyl ether and allyl glycidyl ether, a reaction product between sorbitol triallyl ether and allyl glycidyl ether, a reaction product between sorbitol tetraallyl ether and allyl glycidyl ether, a reaction product between sorbitol pentaallyl ether and allyl glycidyl ether, a reaction product between trimethylolpropane monoallyl ether and allyl glycidyl ether, a reaction product between trimethylolpropane diallyl ether and allyl glycidyl ether, a reaction product between pentaerythritol diallyl ether and allyl glycidyl ether, a reaction product between pentaerythritol triallyl ether and allyl glycidyl ether, a reaction product between dipentaerythritol diallyl ether and allyl glycidyl ether, a reaction product between dipentaerythritol triallyl ether and allyl glycidyl ether, a reaction product between dipentaerythritol tetraallyl ether and allyl glycidyl ether, and a reaction product between dipentaerythritol pentaallyl ether and allyl glycidyl ether.

Preferable are the reaction product between erythritol triallyl ether and allyl glycidyl ether, the reaction product between xylitol triallyl ether and allyl glycidyl ether, the reaction product between sorbitol pentaallyl ether and allyl glycidyl ether, the reaction product between pentaerythritol triallyl ether and allyl glycidyl ether, the reaction product between trimethylolpropane diallyl ether and allyl glycidyl ether, the reaction product between dipentaerythritol pentaallyl ether and allyl glycidyl ether.

In another embodiment of the present invention, the polyallyl ether compound (A-1) having no oxyethylene chain is of the general formula:

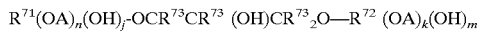

wherein $R^{71}$ and $R^{72}$ are a linear or branched $C_1-C_{10}$ hydrocarbon group optionally intervened by an ether oxygen atom, each $R^{73}$ is, the same or different, a hydrogen atom, a linear or branched alkyl group or a halogen atom, k and n are a number of at least 1, and m and j are at least 0.

Such polyallyl ether compound (A-1) can be prepared, for example, by reacting an allyl group-containing epoxy compound of the general formula:

$$GOR^{72}(OA)_k(OH)_m$$

wherein

G is a glycidyl group, $R^{71}$ is a linear or branched $C_1-C_{10}$ hydrocarbon group optionally intervened by an ether oxygen atom, A is an allyl group, m is a whole number of at least 0, and k is from 1 to (r-1), with an allyl group-containing alcohol of the general formula:

wherein $R^{71}$ a linear or branched $C_1-C_{10}$ hydrocarbon group optionally intervened by an ether oxygen atom, x is a whole number of at least 2, n is a whole number of from 1 to (x-1), said allyl group-containing epoxy compound being a monoglycidyl ether and allyl ether of a polyol represented by the general formula:

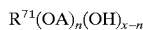

wherein $R^{72}$ is a linear or branched $C_1-C_{10}$ hydrocarbon group optionally intervened by an ether oxygen atom, y is a whole number of at least 2, and said allyl group-containing alcohol being prepared by allyl-etherifying a polyol of the general formula:

wherein $R^{71}$ a linear or branched $C_1-C_{10}$ hydrocarbon group optionally intervened by an ether oxygen atom, and x is a whole number of at least 2.

y and x may be, for example, from 2 to 10, particularly from 2 to 6. m and j may be at least 0, for example, from 0 to 8. (n+k) may be at least 2, particularly at least 3, for example, from 3 to 6. Preferable examples of n and k are 1, 2, 3, 4 and 5.

Examples of $R^{71}(OH)_y$ and $R^{72}(OH)_x$ are erythritol, xylitol, sorbitol, trimethylolpropane, pentaerythritol and dipentaerythritol.

Specific examples of such polyallyl ether compound (that is, a compound having hydrocarbon groups at both ends) are as follows:

a reaction product of an epoxy compound which is allyl glycidyl ether with an allyl group-containing alcohol which is selected from sorbitol triallyl ether, trimethylolpropane diallyl ether, or pentaerythritol triallyl ether; and a reaction product of an epoxy compound which is selected from trimethanolpropane diallyl ether glycidylether or pentaerythritol triallyl ether glycidylether, with an allyl group-containing alcohol which is trimethylolpropane diallyl ether or pentaerythritol triallyl ether.

The following method is generally used to prepare a crosslinking agent comprising an addition-reaction product between the epoxy compound and the allyl group-containing alcohol.

One part by mol of an allyl group-containing epoxy compound of the general formula:

wherein

G is a glycidyl group, and

A is an allyl group, or an allyl group-containing epoxy compound of the general formula:

wherein

G is a glycidyl group, $R^{72}$ is a linear or branched $C_1-C_{10}$ alkyl group optionally intervened by an ether oxygen atom, A is an allyl group, k is from 1 to (y-1), and m is a whole number of at least 0, and 5 to 10 parts by mol of an allyl group-containing alcohol of the general formula:

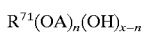

wherein $R^{71}$ is a linear or branched alkyl group optionally intervened by an ether oxygen atom, and may be the same as or different from $R^{72}$, x is a whole number of at least 2, n is a whole number of from 1 to (x-1) provided that (n+k) is at least 2, in which the allyl group-containing alcohol is prepared by allyl-etherifying a polyol of the general formula:

$$R^{71}(OH)_x$$

wherein
R$^{71}$ is a linear or branched alkyl group optionally intervened by an ether oxygen atom, and may be the same as or different from R$^{72}$,
x is a whole number of at least 2,
are charged into a suitable reaction vessel equipped with a stirrer, a thermometer and a reflux condenser. The mixture is heated at about 50 to 150° C. under stirring. A catalyst (for example, nickel sulfate, copper sulfate, iron (III) sulfate, a boron trifluoride ether complex, a quaternary ammonium salt, crown ether/alkali metal hydroxide are mentioned.) is added and the reaction is conducted for 1 to 3 hours. After the completion of the reaction, the unreacted allyl group-containing alcohol is distilled off and then the resulting product may be purified by conventional techniques such as distillation, extraction, recrystallization and liquid chromatography.

Hereinafter, a polyallyl ether compound (A-2) having oxyethylene chain is explained.

The polyallyl ether compound (A-2) having oxyethylene chain is preferably of the general formula:

$$R\text{—}OCH_2CH(OH)CH_2\ O(CH_2\ CH_2O)_n\ CH_2\ CH(OH)CH_2\ O\text{—}R$$

wherein
each R is, the same or different, a hydrocarbon group optionally having an ether oxygen atom and/or an allyl group (provided that the total number of allyl groups in two R groups is at least 2, and wherein one R group has 1 to 15 carbon atoms.), and
n is a number of at least 1.

The R group may be a group having no hydroxyl group. The R group may be an alkyl group having at least one oxyallyl group.

The polyallyl ether compound (A-2) having oxyethylene chain is generally prepared by the reacting an allyl-group containing alcohol with an ethyleneglycol diglycidyl ether compound.

The allyl group-containing alcohol can be prepared by allyl-etherifying at least one hydroxyl group of a polyol compound having at least two hydroxyl groups. The allyetherification reaction can be conducted by means of an allyl-etherifying agent. In the allyl-etherification reaction of the polyol compound, a hydrogen atom of the hydroxyl group in the polyol compound is substituted by an allyl group.

The polyol compound has at least 2, for example 3 to 10 hydroxyl groups. The polyol compound may be of the general formula:

$$R^1(OH)_m$$

wherein
R$^1$ is a linear or branched C$_1$–C$_{12}$ (particularly C$_1$–C$_{12}$ hydrocarbon group (for example, an alkyl group) optionally having an ether oxygen atom, and
m is a number of at least 2.

Specific examples of the polyol compound is a linear compound having 2 to 12, for example 4 to 10 carbon atoms (for example, ethyleneglycol, glycerin, erythritol, xylitol and sorbitol), a branched compound having 4 to 12 carbon atoms (for example, pentaerythritol, dipentaerythritol and trimethylolpropane), or a cyclic compound having 4 to 12 carbon atoms (for example, glucose, fructose, maltose, sucrose and lactose).

The allyl-etherifying agent is a compound having an allyl group and a reactive group. The allyl group and the reactive group may be bonded by means of a direct bond, or may be a divalent organic group (for example, a substituted or unsubstituted hydrocarbon group (having, for example, 1 to 10 carbon atoms). Usually, the allyl-etherifying agent consists of one allyl group, and one reactive group bonded to the allyl group by a direct bond.

Examples of the reactive group in the allyl-etherifying agent are a halogen atom, an alkyl sulfonyloxy group (the number of carbon atoms in the alkyl group is, for example, from 1 to 10.), aryl sulfonyloxy group (the number of carbon atoms in the aryl group is, for example, from 6 to 20.), aralkyl sulfonyloxy group (the number of carbon atoms in the aralkyl group is, for example, from 7 to 30.).

Examples of the halogen atom include chlorine and bromine.

Examples of the alkyl sulfonyloxy group include a methyl sulfonyloxy 5 group, an ethyl sulfonyloxy group, a n-propyl sulfonyloxy group, an isopropyl sulfonyloxy group, a n-butyl sulfonyloxy group, a n-octyl sulfonyloxy group, a trifuloromethane sulfonyloxy group, a trichloromethane sulfonyloxy group, a 2-chloro-1-ethane sulfonyloxy group, a 2,2,2-trifluoroethane sulfonyloxy group, a 3-chloropropane sulfonyloxy group, and a perfluoro-1-butane sulfonyloxy group.

Examples of the aryl sulfonyloxy group include a benzene sulfonyloxy group, a 2-aminobenzene sulfonyloxy group, a 2-nitrobenzene sulfonyloxy group, a 2-methoxycarbonyl benzene sulfonyloxy group, a 3-aminobenzene sulfonyloxy group, a 3-nitrobenzene sulfonyloxy group, a 3-methoxycarbonyl benzene sulfonyloxy group, a p-toluene sulfonyloxy group, a 4-tert-butyl benzene sulfonyloxy group, a 4-fluorobenzene sulfonyloxy group, a 4-chlorobenzene sulfonyloxy group, a 4-bromobenzene sulfonyloxy group, a 4-iodobenzene sulfonyloxy group, a 4-methoxybenzene sulfonyloxy group, a 4-aminobenzene sulfonyloxy group, a 4-nitrobenzene sulfonyloxy group, a 2,5-dichlorobenzene sulfonyloxy group, a pentafluorobenzene sulfonyloxy group, a 1-naphthalene sulfonyloxy group, and a 2-naphthalene sulfonyloxy group.

Examples of the aralkyl sulfonyloxy group include an α-toluene sulfonyloxy group, a trans-p-styrene sulfonyloxy group, and a 2-nitro-α-toluene sulfonyloxy group.

Examples of the allyl-etherifying agent include an allyl halide, an alkyl sulfonyloxyallyl, an aryl sulfonyloxyallyl, and an aralkyl sulfonyloxyallyl.

Examples of the allyl halide include allyl chloride and allyl bromide.

Examples of the alkyl sulfonyloxyallyl include methyl sulfonyloxyallyl, ethyl sulfonyloxyallyl, n-propyl sulfonyloxyallyl, isopropyl sulfonyloxyallyl, n-butyl sulfonyloxyallyl, n-octyl sulfonyloxyallyl, trifluoromethane sulfonyloxyallyl, trichloromethane sulfonyloxyallyl, 2-chloro-1-ethane sulfonyloxyallyl, 2,2,2-trifluoroethane sulfonyloxyallyl, 3-chloropropane sulfonyloxyallyl, and perfluoro-1-butane sulfonyloxyallyl.

Examples of the aryl sulfonyloxyallyl include benzene sulfonyloxyallyl, 2-aminobenzene sulfonyloxyallyl, 2-nitrobenzene sulfonyloxyallyl, 2-methoxycarbonyl benzene sulfonyloxyallyl, 3-aminobenzene sulfonyloxyallyl, 3-nitrobenzene sulfonyloxyallyl, 3-methoxycarbonylbenzene sulfonyloxyallyl, p-toluene sulfonyloxyallyl, 4-tert-butyl benzene sulfonyloxyallyl, 4-fluorobenzene sulfonyloxyallyl, 4-chlorobenzene sulfonyloxyallyl, 4-bromobenzene sulfonyloxyallyl, 4-iodobenzene sulfonyloxyallyl, 4-methoxybenzene sulfonyloxyallyl, 4-aminobenzene sulfonyloxyallyl, 4-nitrobenzene sulfonyloxyallyl, 2,5-dichlorobenzene sulfonyloxyallyl, pentafluorobenzene sulfonyloxyallyl, 1-naphthalene sulfonyloxyallyl, and 2-naphthalene sulfonyloxyallyl.

Examples of the aralkyl sulfonyloxyallyl include α-toluene sulfonyloxyallyl, trans-β-styrene sulfonyloxyallyl and 2-nitro-α-toluene sulfonyloxyallyl.

The allyl group-containing alcohol is a compound having at least one allyl group and at least one hydroxyl group. The allyl group-containing alcohol is preferably of the general formula:

$$(AO)_l R^1 (OH)_{m-1}$$

wherein

A is an allyl group,

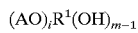 is a number of at least one, and $R^1$ and m are the same as defined above.

The number of hydroxyl groups in the allyl group-containing alcohol is preferably 1. The allyl group-containing alcohol is preferably trimethylolpropane diallyl ether or pentaerythritol tiallyl ether.

The following method is generally used to prepare the allyl group-containing ether by allyl-etherification of the polyol compound.

One part by mol of the polyol compound, y part by mol of potassium hydroxide or sodium hydroxide, and 10 to 50 wt-% of water or an aprotic polar solvent (e.g. acetonitrile, tetrahydrofuran, dioxane, and dimethyl formaldehyde) are introduced into a suitable reaction vessel equipped with a stirrer, a thermometer and a reflux condenser. The mixture is heated at about 50 to 150° C. under stirring, then y part by mol of the allyl-etherifying agent is added dropwise, and the mixture is reacted for about 2 to 10 hours. After the completion of the reaction, the resulting liquid layer is separated from the precipitated solid and purified by conventional techniques such as distillation, extraction, recrystallization and liquid chromatography. Sodium hydroxide or potassium hydroxide may be added dropwise as an aqueous solution to the reaction system, simultaneously with adding the allyl-etherifying agent.

The polyallyl ether compound (A-2) of the present invention can be prepared by reacting the allyl group-containing alcohol with an ethyleneglycol diglycidyl ether compound.

The ethyleneglycol diglycidyl ether compound is a compound having an ethyleneglycol chain ($-O(CH_2\ CH_2O)_n-$) having two ends each bonded to a glycidyl group. The ethyleneglycol diglycidyl ether compound is preferably of the formula:

$$GO\text{-}(CH_2\ CH_2O)_n\text{-}G$$

wherein

G is a glycidyl group, and

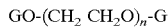 is a whole number of at least 1.

n is, for example, from 1 to 20, preferably from 1 to 10, particularly from 1 to 4.

The following method is generally used to prepare the polyallyl ether compound (A-2) from the allyl group-containing alcohol and the ethyleneglycol diglycidyl ether compound.

One part by mol of ethyleneglycol diglycidyl ether compound and 5 to 10 parts by mol of an allyl group-containing alcohol were charged into a suitable reaction vessel equipped with a stirrer, a thermometer and a reflux condenser. The mixture is heated at about 50 to 150° C. under stirring. A catalyst (for example, nickel sulfate, copper sulfate, iron (III) sulfate, a boron trifluoride ether complex, a quaternary ammonium salt, crown ether/alkali metal hydroxide are mentioned.) is added and the reaction is conducted for about 1 to 3 hours. After the completion of the reaction, the unreacted allyl group-containing alcohol is distilled off and then the resulting product may be purified by conventional techniques such as distillation, extraction, recrystallization and liquid chromatography.

In production of a highly water-absorbing polymer, the crosslinking agent of the present invention is used for crosslinking said polymer. Generally, a highly water-absorbing polymer is crosslinked in an aqueous medium with the crosslinking agent of the present invention.

Generally, the crosslinking agent of the present invention is used in the production of a highly water-absorbing polymer polymerized in an aqueous medium and comprising a polymerizable compound having a carbon-carbon double bond or a salt thereof. In production of the highly water-absorbing polymer, said polymerizable compound and/or a salt thereof can be used as the monomer.

A repeating unit in the highly water-absorbing polymer has a functional group. Examples of the functional group include a carboxyl group, a hydroxyl group, an amide group and an acetamide group.

Examples of the highly water-absorbing polymer include an acrylic acid-based polymer, a vinyl alcohol-based polymer, an isobutylene/maleic anhydride-based polymer, an acrylamide-based polymer, an acrylamide/acrylic acid-based polymer, and a N-vinyl acetamide-based polymer. Generally, a monomer forming the highly water-absorbing polymer has the functional group. In production of a certain polymer such as polyvinyl alcohol, however, a vinyl ester such as vinyl acetate or vinyl propionate may be used as the monomer, and then a functional group such as a hydroxyl group may be introduced into the sythesized polymer.

Examples of the monomer forming the highly water-absorbing polymer include acrylic acid, methacrylic acid, maleic acid, fumaric acid, itaconic acid, crotonic acid, citraconic acid, α-hydroxyacrylic acid, aconitic acid, 2-(meth)acryloylethane sulfonic acid, 2-(meth)acrylamide-2-methylpropane sulfonic acid and salts thereof. Examples of the salts include metal salts. Examples of metals in the salts are alkali metals (e.g. potassium and sodium).

The crosslinking agent is preferably dissolved in a mixture of the monomer and an aqueous medium. The solubility of the crosslinking agent in 100 mL of the mixture of the monomer and the aqueous medium is at least 0.2 g, for example at least 0.4 g. The aqueous medium consists of water only or comprises water and a water-soluble organic solvent (e.g. alcohol).

The highly water-absorbing polymer may be based on a complete or partial salt of carboxylic acid.

The crosslinking agent of the present invention can be used in any methods known in the art, which are not limited. For example, 60 to 90 mol-% of an aqueous solution of an acrylic acid monomer is neutralized with e.g. an aqueous solution of sodium hydroxide to form 30 to 50 weight-% aqueous solution, then the crosslinking agent is mixed in an amount of 0.1 to 1.0 weight-%, a redox radical polymerization initiator such as an azo compound or a peroxide is added thereto, the monomer is polymerized usually at a temperature of 100° C. or less, and the formed polymer is cut into pieces having a suitable size and then dried, whereby the highly water-absorbing polymer can be produced (a method of polymerization after neutralization).

Alternatively, the crosslinking agent and the polymerization initiator are added to an aqueous solution of an acrylic acid monomer not neutralized, then the monomer is polymerized, and the formed solid is cut into pieces of suitable size and neutralized with sodium hydroxide (a method of polymerization before neutralization).

PREFERRED EMBODIMENTS OF THE INVENTION

Hereinafter, the present invention is described in more detail with reference to the Examples and Comparative Examples.

The water absorptivity of a powdery polymer (amount of absorbed water (g) per 1 g of a powdery polymer) was evaluated in the following manner.

About 0.2 g powdery polymer is accurately weighed, introduced uniformly into a tea bag-type bag made of non-woven fabric (6.8 mm×9.6 mm), and immersed in a 0.9% saline solution, and the weight thereof after immersed for 1 hour is measured. Taking that the weight of the bag only is the blank, the water absorptivity of the powdery polymer is calculated according to the following equation:

Water absorptivity=[(weight (g) after water absorption)−(blank (g)))]/[weight (g) of highly water-absorbing polymer]

(1) Production of a crosslinking agent

EXAMPLE 1

850 g of trimethylolpropane diallyl ether and 140 g of allyl glycidyl ether were introduced into a 2 L reactor equipped with a thermometer, an agitator and a reflex condenser, and then 1.5 g of a boron trifluoride/diethyl ether complex was added to conduct the reaction at 60° C. for 2 hours. The reaction was monitored by a liquid chromatography (analytical conditions were as follows: column: ODS-120-5-AP manufactured by Daiso Co., Ltd., column temperature: 25° C., eluent: methanol/water (4:1) at a flow rate of 1 mL/min.). After the disappearance of allyl glycidyl ether was confirmed, the reaction was discontinued. The resultant reaction mixture was vacuum concentrated (at 0.7 mmHg and 160° C.). The residue (reaction product) was subjected to $^1$H NMR, an element analysis, a iodine value measurement and hydroxyl group value measurement and was confirmed to be a compound of he following Chemical Formula 1.

The solubility of this compound in an aqueous acrylic acid solution partially neutralized with sodium hydroxide was determined in the following manner.

180 g of acrylic acid, 75 g of sodium hydroxide, and 424 g of distilled water were mixed to prepare a standard aqueous solution of acrylate salt having a monomer concentration of 32.4% by weight and a degree of neutralization of 75% by mol.

10 g of the mixture obtained in the above experiment was added to 100 g of the standard aqueous solution of acrylate salt, then shaken vigorously and left to be separated into 2 layers, and an aqueous layer was removed and analyzed by a liquid chromatography (analytical conditions were as follows: column: ODS-120-5-AP manufactured by Daiso Co., Ltd., column temperature: 25° C., eluent: methanol/water (4:1) at a flow rate of 1 mL/min.), indicating that the solubility was 0.91 w/v %.

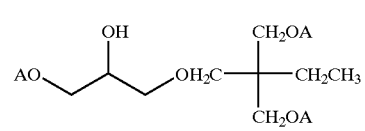

Chemical Formula 1 wherein A is an allyl group.

EXAMPLE 2

950 g of pentaerythritol triallyl ether and 140 g of allyl glycidyl ether were introduced into a 2 L reactor equipped with a thermometer, an agitator and a reflex condenser, and then 1.5 g of a boron trifluoride/diethyl ether complex was added to conduct the reaction at 60° C. for 2 hours. The reaction was monitored by a liquid chromatography (analytical conditions were as follows: column: ODS-120-5-AP manufactured by Daiso Co., Ltd., column temperature: 25° C., eluent: methanol/water (4:1) at a flow rate of 1 ml/min.). After the disappearance of allyl glycidyl ether was confirmed, the reaction was discontinued. The resultant reaction mixture was vacuum concentrated (at 0.7 mmHg and 160° C.). The residue (reaction product) was subjected to $^1$H NMR, an element analysis, a iodine value measurement and a hydroxyl group value measurement and was confirmed to be a compound of the following Chemical Formula 2.

The solubility of this compound in an aqueous solution of acrylic acid partially neutralized by sodium hydroxide was determined in the same manner as in Example 1. The solubility was 0.71 w/v %.

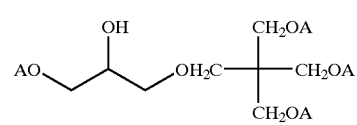

Chemical Formula 2 wherein A is an allyl group.

EXAMPLE 3

850 g of trimethylolpropane diallyl ether and 100 g of epichlorohydrin were introduced into a 2 L reactor equipped with a thermometer, an agitator and a reflex condenser, and then 1.5 g of a boron trifluoride/diethyl ether complex was added to conduct the reaction at 60° C. for 2 hours. The reaction was monitored by a liquid chromatography (analytical conditions were as follows: column: ODS-120-5-AP manufactured by Daiso Co., Ltd., column temperature: 25° C., eluent: methanol/water (4:1) at a flow rate of 1 mL/min.). After the disappearance of epichlorohydrin was confirmed, the reaction was discontinued. 400 mL of a 10 N aqueous solution of sodium hydroxide was added to the resultant reaction mixture and the reaction was conducted 60° for 4 hours. The liquid chromatograph having the conditions shown in Example 2 indicated that the elimination of hydrogen chloride and the ring-closing reaction were completed. The reaction mixture was de-watered. It was confirmed that the water content of resultant product was at most 0.1% by a Karl-Fischer water content measuring machine. Then, 1.5 g of a boron trifluoride/diethyl ether complex was added to react the mixture at 60C for 2 hours. After the completion of the reaction, the unreacted trimethylolpropane diallyl ether was distilled off by a vacuum concentration. The residue (reaction product) was subjected to ¹H NMR, an element analysis, a iodine value measurement and a hydroxyl group value measurement and was confirmed to be a compound of the following Chemical Formula 3.

The solubility of this compound in an aqueous solution of acrylic acid partially neutralized by sodium hydroxide was determined in the same manner as in Example 1. The solubility was 0.41 w/v %.

Chemical Formula 3

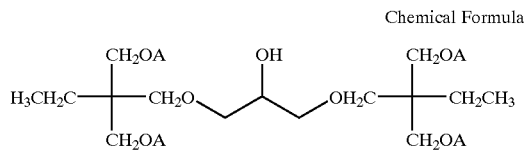

wherein A is an allyl group.

EXAMPLE 4

1,200 g of pentaerythritol triallyl ether and 100 g of epichlorohydrin were introduced into a 2 L reactor equipped with a thermometer, an agitator and a reflex condenser, and then 1.5 g of a boron trifluoride/diethyl ether complex was added to conduct the reaction at 60° C. for 2 hours. The reaction was monitored by a liquid chromatography (analytical conditions were as follows: column: ODS-120-5-AP manufactured by Daiso Co., Ltd., column temperature: 25° C., eluent: methanol/water (4:1) at a flow rate of 1 mL/min.). After the disappearance of epichlorohydrin was confirmed, the reaction was discontinued. 400 mL of a 10 N aqueous solution of sodium hydroxide was added to the resultant reaction mixture and the reaction was conducted at 60° for 4 hours. The liquid chromatograph having the conditions shown in Example 2 indicated that the elimination of hydrogen chloride and the ring-closing reaction were completed. The reaction mixture was de-watered. It was confirmed that the water content of the resultant product was at most 0.1% by a Karl-Fischer water content measuring machine. Then, 1.5 g of a boron trifluoride/diethyl ether complex was added to react the mixture at 60° C. for 2 hours. After the completion of the reaction, the unreacted pentaerythritol triallyl ether was distilled off by a vacuum concentration. The residue (reaction product) was subjected to ¹H NMR, an element analysis, a iodine value measurement and a hydroxyl group value measurement and was confirmed to be a compound of the following Chemical Formula 4.

Chemical Formula 4

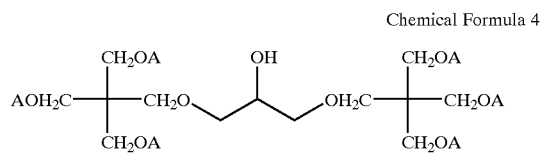

wherein A is an allyl group.

EXAMPLE 5

1,226 g of trimethylolpropane diallyl ether and 252 g of ethylene glycol diglycidyl ether were introduced into a 3 L reactor equipped with a reflex condenser, a thermometer and a mechanical stirrer, and then 1.42 g of a boron trifluoride/diethyl ether complex was added to conduct the reaction at 60° C. for 3 hours. The reaction was monitored by a liquid chromatography (analytical conditions were as follows: column: ODS-120-5-AP manufactured by Daiso Co., Ltd., column temperature: 25° C., eluent: methanol/water (4:1) at a flow rate of 1 mL/min.). After the disappearance of ethylene glycol diglycidyl ether was confirmed, the reaction was discontinued. The resultant reaction mixture was vacuum concentrated (at 0.7 mmHg and 160° C.). The residue (reaction product) was subjected to ¹H NMR, an element analysis, a iodine value measurement and a hydroxyl group value measurement and was confirmed to be a compound of the following Chemical Formula 5.

Chemical Formula 5

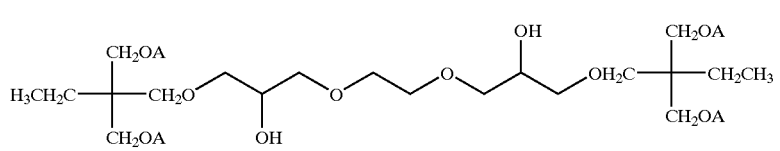

wherein A is an allyl group.

The solubility of this compound in an aqueous solution of acrylic acid partially neutralized by sodium hydroxide was determined in the following manner.

180 g of acrylic acid, 75 g of sodium hydroxide, and 424 g of distilled water were mixed to prepare a standard aqueous solution of acrylate salt having a monomer concentration of 32.4% by weight and a degree of neutralization of 75% by mol.

10 g of the mixture obtained in the above experiment was added to 100 g of the standard aqueous solution of acrylate salt, then shaken vigorously and left to be separated into 2 layers, and an aqueous layer was removed and analyzed by a liquid chromatography (analytical conditions were as follows: column: ODS-120-5-AP manufactured by Daiso Co., Ltd., column temperature: 25° C., eluent: methanol/water (4:1) at a flow rate of 1 mL/min.), indicating that the solubility was 0.91 w/v %.

EXAMPLE 6

1,538 g of pentaerythritol triallyl ether and 252 g of ethylene glycol diglycidyl ether were introduced into a 3 L reactor equipped with a reflex condenser, a thermometer and a mechanical stirrer, and then 1.42 g of a boron trifluoride/diethyl ether complex was added to conduct the reaction at 60° C. for 3 hours. The reaction was monitored by a liquid chromatography (analytical conditions were as follows: column: ODS-120-5-AP manufactured by Daiso Co., Ltd., column temperature: 25° C., eluent: methanol/water (4:1) at a flow rate of 1 mL/min.). After the disappearance of ethylene glycol diglycidyl ether was confirmed, the reaction was discontinued. The resultant reaction mixture was vacuum concentrated (at 0.7 mmHg and 160° C.). The residue (reaction product) was subjected to $^1$H NMR, an element analysis, a iodine value measurement and a hydroxyl group value measurement and was confirmed to be a compound of the following Chemical Formula 6.

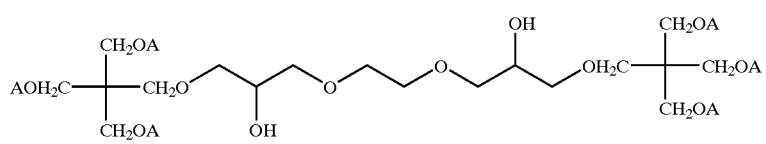

Chemical Formula 6 wherein A is an allyl group.

The solubility of this compound in an aqueous solution of acrylic acid partially neutralized by sodium hydroxide was determined in the same manner as in Example 5. The solubility was 0.87 w/v %.

COMPARATIVE EXAMPLE 1

10 g of trimethylol propane triacrylate was mixed with 100 g of the standard aqueous solution of acrylate salt, then shaken vigorously and left to be separated into 2 layers, and an aqueous layer was removed and analyzed by a gas chromatography (analytical conditions were as follows: column: 30 m, BP20-0.25 manufactured by SGE Co., Ltd., column temperature: from 100 to 200° C. at a temperature increase of 10C/min.), indicating that the solubility was 0.20 w/v %.

The solubilities in the standard aqueous solution of acrylate salt in the above Examples and Comparative Example are summarized in Table 1.

TABLE 1

|  | Ex. 1 | Ex. 2 | Ex. 3 | Ex. 4 | Ex. 5 | Ex. 6 | Com. Ex. 1 |
|---|---|---|---|---|---|---|---|
| Solubility (%(w/v)) | 0.91 | 0.71 | 0.41 | 0.43 | 0.91 | 0.87 | 0.20 g |

The compounds in Examples 1–6 were superior in the solubility in the standard aqueous solution of acrylate salt to the compound in Comparative Example 1.

(2) Production of a highly water-absorbing polymer

EXAMPLE 7

180 g (2.5 mol) of acrylic acid, 75 g (1.875 mol) of NaOH, 424 mL of water and 1.57 g (4.78 mmol) of the compound obtained in Example 1 were introduced into a 1 L separable flask equipped with a nitrogen inlet (for use in liquid and gaseous phase), a thermometer, a dropping funnel and a mechanical stirrer, and the mixture was cooled to a temperature of 5° C. on ice. The mixture at this stage was a colorless transparent liquid having a pH value of 5 to 6. The separable flask was placed in a thermal insulating container, and then a solution of 150 mg (0.56 mmol) 2,2'-azobis(2-amidinopropane) dihydrochloride in 1 mL water, a solution of 20 mg (0.113 mmol) L-ascorbic acid in 1 mL water and a solution of 100 mg (0.91 mmol) of 31% aqueous hydrogen peroxide in 1 mL water were added thereto successively within 1 minute. Just after these materials were added, the turbidity of the mixture was increased, and the viscosity was increased in an exothermic reaction to terminate stirring. The reaction mixture was left for 21 minutes so that it reached the maximum temperature (82° C.). Thereafter, the reaction mixture was left and gradually cooled to room temperature, and the resulting colorless transparent gel was removed from the flask. Apart (about 100 g) of this gel was removed and divided by a speed cutter. When the size of the resulting particles was reduced to about 1 mm or less, the particles were dried for 5 hours in an oven at 180° C. The resulting solids were removed from the oven to give 28.5 g of pale yellow solids. These were ground into powder in a sample mill, placed again in the oven (180° C.), and dried for 5 hours. After 26.2 g of pale yellow powder was thus obtained, the powder was sieved to give 22.3 g of powder having a particle diameter of at least 60 μm. The powdery polymer thus prepared was evaluated for water absorptivity. The water absorptivity was 46 g/g.

EXAMPLE 8

A powdery polymer was prepared in the same manner as in Example 7 except that 1.33 g (3.59 mmol) of the compound obtained in Example 2 was used instead of 1.57 g (4.78 mmol) of the compound obtained in Example 1. The water absorptivity was 47 g/g.

EXAMPLE 9

A powdery polymer was prepared in the same manner as in Example 7 except that 1.74 g (3.59 mmol) of the compound obtained in Example 3 was used instead of 1.57 g (4.78 mmol) of the compound obtained in Example 1. The water absorptivity was 45 μg.

EXAMPLE 10

A powdery polymer was prepared in the same manner as in Example 7 except that 1.36 g (2.39 mmol) of the compound obtained in Example 4 was used instead of 1.57 g (4.78 mmol) of the compound obtained in Example 1. The water absorptivity was 48 g/g.

COMPARATIVE EXAMPLE 2

A powdery polymer was prepared in the same manner as in Example 7 except that 1.41 g (4.78 mmol) of trimethyl propane triacrylate was used instead of 1.57 g (4.78 mmol) of the compound obtained in Example 1. The 15 water absorptivity was 36 g/g.

EXAMPLE 11

180 g (2.5 mol) of acrylic acid, 487 mL of water and 1.57 g (4.78 mmol) of the compound obtained in Example 1 were introduced into a 1 L separable flask equipped with a nitrogen inlet (for use in liquid and gaseous phase), a thermometer, a dropping funnel and a mechanical stirrer, and the mixture was cooled to a temperature of 5° C. on ice. The mixture at this stage was a colorless transparent liquid: The separable flask was placed in a thermal insulating container, and then a solution of 150 mg (0.56 mmol) 2,2'-azobis(2-amidinopropane) dihydrochloride in 1 mL water, a solution of 20 mg (0.113 mmol) L-ascorbic acid in 1 mL water and a solution of 100 mg (0.91 mmol) of 31% aqueous hydrogen peroxide in 1 mL water were added thereto successively within 1 minute. Just after these materials were added, the turbidity of the mixture was increased, and the viscosity was increased in an exothermic reaction to terminate stirring. The reaction mixture was left for 20 minutes so that it reached the maximum temperature (83° C.). Thereafter, the reaction mixture was left and gradually cooled to room temperature, and the resulting colorless transparent gel was removed from the flask.

A part (about 100 g) of this gel was removed and divided by a speed cutter. When the size of the resulting particles was reduced to about 1 mm or less, 23.5 g of 48% aqueous sodium hydroxide solution was added thereto, and the particles were further divided for 30 minutes. The resulting divided gel mixture was dried for 5 hours in an oven at 180° C. to give 28.56 g of pale yellow solids. These were ground into powder in a sample mill, placed again in the oven (180° C.), and dried for 1.5 hours. After 26.2 g of pale yellow powder was thus obtained, the powder was sieved to give 23.2 g of powder having a particle diameter of at least 60 μm.

The powdery polymer thus prepared was evaluated for water absorptivity, indicating that the water absorptivity was 46 gIg.

EXAMPLE 12

180 g (2.5 mol) of acrylic acid, 75 g (1.875 mol) of NaOH, 424 mL of water and 2.16 g (3.59 mmol) of the compound obtained in Example 5 were introduced into a 1 L separable flask equipped with a nitrogen inlet (for use in liquid and gaseous phase), a thermometer, a dropping funnel and a mechanical stirrer, and the mixture was cooled to a temperature of 5° C. on ice. The mixture at this stage was a colorless transparent liquid having a pH value of 5 to 6. The separable flask was placed in a thermal insulating container, and then a solution of 150 mg (0.56 mmol) 2,2'-azobis(2-amidinopropane) dihydrochloride in 1 mL water, a solution of 204 mg (0.113 mmol) L-ascorbic acid in 1 mL water and a solution of 100 mg (0.91 mmol) of 31% aqueous hydrogen peroxide in 1 mL water were added thereto successively within 1 minute. Just after these materials were added, the turbidity of the mixture was increased, and the viscosity was increased in an exothermic reaction to terminate stirring. The reaction mixture was left for 21 minutes so that it reached the maximum temperature (82° C.). Thereafter, the reaction mixture was left and gradually cooled to room temperature, and the resulting colorless transparent gel was removed from the flask. A part (about 100 g) of this gel was removed and divided by a speed cutter. When the size of the resulting particles was reduced to about 1 mm or less, the particles were dried for 5 hours in an oven at 180° C. The resulting solids were removed from the oven to give 28.5 g of pale yellow solids. These were ground into powder in a sample mill, placed again in the oven (180° C.), and dried for 1.5 hours. After 26.2 g of pale yellow powder was thus obtained, the powder was sieved to give 22.3 g of powder having a particle diameter of at least 60 μm.

The powdery polymer thus prepared was evaluated for water absorptivity. The water absorptivity was 46 g/g.

EXAMPLE 13

A powdery polymer was prepared in the same manner as in Example 12 except that 1.64 g (2.39 mmol) of the compound obtained in Example 6 was used instead of 2.16 g (3.59 mmol) of the compound obtained in Example 5. The water absorptivity of the powdery polymer was measured and was 46 g/g.

EXAMPLE 14

180 g (2.5 mol) of acrylic acid, 487 mL of water and 2.16 g (3.59 mmol) of the compound obtained in Example 5 were introduced into a 1 L separable flask equipped with a nitrogen inlet (for use in liquid and gaseous phase), a thermometer, a dropping funnel and a mechanical stirrer, and the mixture was cooled to a temperature of 5° C. on ice. The mixture at this stage was a colorless transparent liquid. The separable flask was placed in a thermal insulating container, and then a solution of 150 mg (0.56 mmol) 2,2'-azobis(2-amidinopropane) dihydrochloride in 1 mL water, a solution of 20 mg (0.113 mmol) L-ascorbic acid in 1 mL water and a solution of 100 mg (0.91 mmol) of 31% aqueous hydrogen peroxide in 1 mL water were added thereto successively within 1 minute. Just after these materials were added, the turbidity of the mixture was increased, and the viscosity was increased in an exothermic reaction to terminate stirring. The reaction mixture was left for 20 minutes so that it reached the maximum temperature (83° C.). Thereafter, the reaction mixture was left and gradually cooled to room temperature, and the resulting colorless transparent gel was removed from the flask. A part (about 100 g) of this gel was removed and divided by a speed cutter. When the size of the resulting particles was reduced to about 1 mm or less, 23.5 g of 48% aqueous sodium hydroxide was added thereto, and the particles were further divided for 30 minutes. The resulting divided gel mixture was dried for 5 hours in an oven at 180° C. to give 28.56 g of pale yellow solids. These were ground into powder in a sample mill, placed again in the oven (180° C.), and dried for 1.5 hours. After 26.2 g of pale yellow powder was thus obtained, the powder was sieved to give 23.2 g of powder having a particle diameter of at least 60 μm.

The powdery polymer thus prepared was evaluated for water absorptivity, indicating that the water absorptivity was 46 gIg.

Effect of the Invention

The crosslinking agent of the present invention is industrially valuable and can be used for the production of a highly water-absorbing polymer mainly containing a complete salt or partial salt of a polymer derived from a monomer having a polymerizable double bond or a salt thereof to be polymerized in an aqueous medium. The crosslinking agent of the present invention is satisfactory in the solubility in an aqueous acrylate salt solution and can give an excellent highly water-absorbing polymer. In addition, the crosslinking agent of the present invention can be practically used not only in the method of polymerization before neutralization but also in the method of polymerization after neutralization, and is effective for simplification of the process.

What is claimed is:

1. A crosslinking agent for use in the production of a highly water-absorbing polymer comprising a polymerizable compound having a carbon-carbon double bond or a salt thereof, said crosslinking agent comprising a polyallyl ether compound having at least two allyl groups and at least one hydroxyl group derived from a glycidyl group, and said polyallyl ether compound being:

(A-1) a polyallyl ether compound having at least two allyl groups and at least one hydroxyl group derived from a glycidyl group, and having no oxyethylene chain, and/or (A-2) a polyallyl ether compound having at least two allyl groups and at least one hydroxyl group derived from a glycidyl group, and having at least one oxyethylene chain, which is an addition product between an ethyleneglycol diglycidyl ether compound of the general formula:

G-O-(CH$_2$CH$_2$O)$_n$-G wherein

G is a glycidyl group, and n is a whole number of at least 1, and trimethylolpropane diallyl ether.

2. The crosslinking agent according to claim 1 wherein the highly absorbing polymer is crosslinked in an aqueous medium.

3. The crosslinking agent according to claim 1 wherein the polymerizable compound has also a carboxyl group.

4. The crosslinking agent according to anyone of claims 1 2 or 3 wherein the polyallyl ether compound (A-1) having no oxyethylene chain is a compound of the general formula (I):

R$^1$—OC(R$^3$)$_2$—C(R$^3$)(OH)—C(R$^3$)$_2$ O—R$^2$       (I)

wherein

R$^1$ and R$^2$ are, the same or different, an allyl group, or a hydrocarbon group (the number of carbon atoms in the hydrocarbon group is from 1 to 15) having an allyl group and optionally having an ether oxygen atom and/or a hydroxyl group, and each R$^3$ is, the same or different, a hydrogen atom, a linear or branched alkyl group having 1 to 10 carbon atoms or a halogen atom.

5. The crosslinking agent according to claim 4 wherein, in the general formula (I), the R$^1$ group is a R$^{11}$(OA)$_n$ (OH)$_j$- group and R$^2$ is an A group, wherein R$^{11}$ is a C$_4$–C$_{12}$ hydrocarbon group optionally having an ether oxygen atom, A is an allyl group, n is a number of at least 1, and j is a number of at least 0.

6. The crosslinking agent according to claim 4 wherein, in the general formula (I), the R$^1$ group is a R$^{11}$(OA)$_n$ (OH)$_j$- group and R$^2$ is a —(OA)$_k$ (OH)$_m$ R$^2$ group wherein R$^{11}$ and R$^{12}$ is a C$_4$–C$_{12}$ hydrocarbon group optionally having an ether oxygen atom, A is an allyl group, n and k are a number of at least 1, and j and m is a number of at least 0.

7. The crosslinking agent according to anyone of claims 1, 2 or 3 wherein the polyallyl ether compound (A-1) having no oxyethylene chain is prepared from an epoxy compound and an allyl group-containing alcohol.

8. The crosslinking agent according to claim 7 wherein the epoxy compound is an allyl group-containing epoxy compound of the general formula:

G-O-A       (i)

or the general formula:

G-O—R$^{12}$ (OA)$_k$ (OH)$_m$       (ii), the allyl group-containing alcohol is of the general formula:

R$^{11}$(OA)$_n$(OH)$_{j+1}$ wherein G is a glycidyl group,

R$^{11}$ and R$^{12}$ is a C$_4$–C$_{12}$ hydrocarbon group optionally having an ether oxygen atom, A is an allyl group, n and k are a number of at least 1, and j and m are a number of at least 0.

9. The crosslinking agent according to claim 7 wherein the epoxy compound is allyl glycidyl ether, and the allyl group-containing alcohol is a compound selected from sorbitol triallyl ether, trimethylolpropane diallyl ether or pentaerythritol triallyl ether.

10. The crosslinking agent according to claim 7 wherein the epoxy compound is pentaerythritol triallyl ether glycidyl ether, and the allyl group-containing alcohol is a compound selected from trimethylolpropane diallyl ether or pentaerythritol triallyl ether.

* * * * *